(12) United States Patent
Wu et al.

(10) Patent No.: US 8,029,709 B2
(45) Date of Patent: Oct. 4, 2011

(54) LIQUID CORE CAPSULES AND METHODS OF SYNTHESIS THEREOF THROUGH INTERFACIAL POLYMERIZATION

(75) Inventors: Dan Wu, Cincinnati, OH (US); Charles Scott, Thornhill (CA); Carlos Co, Cincinnati, OH (US); Chia-Chi Ho, Cincinnati, OH (US)

(73) Assignee: The University of Cincinnati, Cincinnati, OH (US)

( * ) Notice: Subject to any disclaimer, the term of this patent is extended or adjusted under 35 U.S.C. 154(b) by 1676 days.

(21) Appl. No.: 11/263,310

(22) Filed: Oct. 31, 2005

(65) Prior Publication Data
US 2006/0127490 A1    Jun. 15, 2006

Related U.S. Application Data

(60) Provisional application No. 60/623,606, filed on Oct. 29, 2004.

(51) Int. Cl.
*B01J 13/02* (2006.01)
*B32B 5/00* (2006.01)

(52) U.S. Cl. .................................. 264/4.1; 428/402

(58) Field of Classification Search ..... 428/402–402.24; 427/213.3–213.36; 264/4–4.7
See application file for complete search history.

(56) References Cited

U.S. PATENT DOCUMENTS

| | | | | |
|---|---|---|---|---|
| 3,740,362 | A * | 6/1973 | Gaylord | 527/312 |
| 4,520,091 | A * | 5/1985 | Kakimi et al. | 430/110.2 |
| 5,051,306 | A * | 9/1991 | Meinard et al. | 428/402.21 |
| 5,108,863 | A * | 4/1992 | Hsieh et al. | 430/110.2 |
| 5,143,954 | A * | 9/1992 | Hutton et al. | 524/106 |
| 5,596,051 | A * | 1/1997 | Jahns et al. | 526/73 |
| 2004/0032038 | A1* | 2/2004 | Ali et al. | 264/4.1 |

FOREIGN PATENT DOCUMENTS

JP    1-319757 A  * 12/1989

OTHER PUBLICATIONS

Chuong Bui et al.; Application of a non-ionic amphiphilic maleic diester as polymerizable surfactant in free-radical emulsion polymerization; Polymer Bulletin; 1999; pp. 287-294; vol. 42; Springer-Verlag.
A. Montoya-Goni et al.; Reactive surfactants in heterophase polymerization. XXIV. Emulsion polymerization of styrene with maleate- and succinate-containing cationic surfactants; Polymer; 1999; pp. 1359-1366; vol. 40; Elsevier Science Ltd.
Patrick Lacroix-Desmazes et al.; Reactive Surfactants in Heterophase Polymerization. 2. Maleate Based Poly(ethylene oxide) Macromonomers as Steric Stabilizer Precursors in the Dispersion Polymerization of Styrene in Ethanol-Water Media; Macromolecules; 1996; pp. 4508-4515; vol. 29, No. 13; ACS Publications.
Alain Guyot et al.; Styrene Emulsion Polymerization in the Presence of a Maleate-Functional Surfactant; Journal of Applied Polymer Science; 1997; pp. 2289-2296; vol. 65; John Wiley & Sons, Inc.
Harold A. S. Schoonbrood, et al.; Reactive Surfactants in Heterophase Polymerization. VIII. Emulsion Polymerization of Alkyl Sulfopropyl Maleate Polymerizable Surfactants (Surfmers) with Styrene; Journal of Polymer Science: Part A: Polymer Chemistry; 1997; pp. 2561-2568; vol. 35; John Wiley & Sons, Inc.

* cited by examiner

*Primary Examiner* — James J Seidleck
*Assistant Examiner* — Saira Haider
(74) *Attorney, Agent, or Firm* — Hahn Loeser & Parks, LLP; John J. Cunniff

(57) ABSTRACT

A process for the encapsulation of liquid particles within nanometer thick polymer shells utilizes an interfacial free radical alternating copolymerization process. Encapsulating a liquid material includes providing a mixture comprising the liquid material to be encapsulated, a hydrophobic monomer in a non-polar solution and a hydrophilic monomer in a polar solution. The liquid material is compatible in either the polar solution or the non-polar solution. The polar solution and the non-polar solution are not miscible in each other. The mixture is homogenized to form an emulsion, and then polymerized by an initiator which initiates an interfacial free radical alternating copolymerization process. The copolymerization process is optimally constrained to proceed only at the hydrophobic and hydrophilic interface thus forming a polymer around the liquid material.

11 Claims, 7 Drawing Sheets

LIQUID CORE CAPSULES AND METHODS OF SYNTHESIS THEREOF THROUGH INTERFACIAL POLYMERIZATION

CROSS REFERENCE TO RELATED APPLICATIONS

This application claims priority from U.S. Provisional Application No. 60/623,606, filed on Oct. 29, 2004.

STATEMENT REGARDING FEDERALLY SPONSORED RESEARCH OR DEVELOPMENT

This invention was made with U.S. government support under cooperative agreements awarded by the National Science Foundation under contract number NSF CTS 0324303. The U.S. government may have certain rights to the invention.

BACKGROUND OF THE INVENTION

This invention relates to the formation of liquid core capsules utilizing interfacial polymerization. More particularly, this invention relates to the encapsulation of liquid particles within nanometer thick polymer shells utilizing an interfacial free radical alternating copolymerization process.

Liquid-core capsules have wide-ranging applications in the high efficiency encapsulation and controlled delivery of drugs, dyes, enzymes, and many other biological substrates. These important applications have driven the rapid development of innovative techniques, based on layer-by-layer assembly, shell polymerization of particles and dendrimers followed by core-removal, microphase separation of core-shell latexes, and vesicles, to confine polymerization or assembly of encapsulants at the interface.

Interfacial polymerizations based on the reactions of amines and acid chlorides, lactide diols and diketene acetals, isocyanates and alcohols, isocyanates and amines, or urea and formaldehyde have been used to form liquid-core polymer capsules. As it stands however, monomers for these polymerizations react immediately upon contact and/or hydrolyze when finely dispersed in water. Thus, capsules smaller than 1 micron are difficult to prepare reliably. Moreover, the chemistry of these step polymerizations intrinsically requires two different chemical functionalities. Choices for a third functionality, e.g., acidic/basic or charged groups to allow for pH/ionic strength control of shell permeability without interfering with the polymerization, are thus very limited.

In traditional free-radical interfacial polymerizations, a macromer solution, which is a polymerizable pre-polymer, that optionally contains a co-catalyst, is applied to a material. The macromer is then polymerized with a free radical initiator that is adsorbed onto the surface of the material to be coated while the non-adsorbed initiator is rinsed off by a rinsing solution or by application of a macromer solution. One example of interfacial polymerization is the Microcapsule Interfacial Polymerization Method. Biological materials can be encapsulated as described above with reference to suspension polymerization, but utilizing interfacial polymerization to form the membrane on the surface of the biological material or microcapsule. This involves coating the biological material or microcapsule with a photoinitiator, suspending the biological material or microcapsules in the macromer solution, and immediately polymerizing the mixture, for example, by irradiating. A thin polymer coat, of less than 50 microns thickness can be formed around the biological materials or the microcapsule since the photoinitiator is present only at the microcapsule surface and is given insufficient time to diffuse far into the macromer solution.

In most cases, the initiator, such as a dye, will penetrate into the interior of the biological material or the microcapsule, as well as adsorbing to the surface. When macromer solution, optionally containing a cocatalyst such as triethanolamine, is applied to the surface and exposed to an initiating agent such as laser light, all the essential components of the reaction are present only at and just inside the interface of the biological material or microcapsule and macromer solution. Hence, polymerization and gelation (if multifunctional macromer is used), which typically occurs within about 100 msec, initially takes place only at the interface, just beneath it, and just beyond it. If left for longer periods of time, initiator starts diffusing from the inner core of the microsphere into the solution; similarly, macromers start diffusing inside the core and a thicker layer of polymer is formed.

Another example of an interfacial polymerization technique is the Direct Interfacial Polymerization Method, which promotes the formation of a membrane directly onto the surface of materials of interest that include, for example, cells and tissue. In this process, the material is directly coated with initiator, excess initiator is removed, the macromer solution is applied to the tissue and then polymerized.

Although encapsulation of materials through the use of interfacial polymerization exists, there is a need for a direct approach to preparing liquid-core capsules capable of controlling the shell thickness using interfacial free radical alternating copolymerization.

SUMMARY OF THE INVENTION

It is, therefore, an aspect of the present invention to provide the encapsulation of liquid core capsules through interfacial polymerization.

It is another aspect of the present invention to provide the encapsulation of submicron liquid particles within nanometer thick polymer shells utilizing an interfacial free radical alternating copolymerization process.

In general, the present invention provides a method of encapsulating a liquid material. The method includes providing a mixture comprising a hydrophobic monomer in a non-polar solvent and a hydrophilic monomer in a polar solvent, and the polar and non-polar solutions are not miscible in each other. Optionally, a liquid material which will preferentially separate into either the polar solution or the non-polar solution may also be provided in the mixture. The mixture is homogenized, such as through the application of a shearing force, to form an emulsion containing droplets of non-polar solution in the polar solution or droplets of polar solution in the non-polar solution. The mixture is then polymerized by an initiator that initiates an interfacial free radical alternating copolymerization process, forming a polymer shell around the liquid material. The copolymerization process may be constrained to proceed only at the non-polar and polar interface, thus forming a polymer shell around the droplets. In this manner, the invention also provides a liquid core capsule comprising a polymer shell that is a reaction product of a hydrophobic monomer and a hydrophilic monomer and a liquid core surrounded by the polymer shell. It is envisioned that a drug delivery system may include such a capsule where a drug is located within the liquid core capsule. It is envisioned that a crosslinked polymer shell may be particularly desirable in some applications.

In a particular embodiment, neither the hydrophobic monomer nor the hydrophilic monomer substantially homopolymerize; homopolymerization is limited to trace amounts. Polymerization ceases when either monomer is exhausted. In this way, the thickness of the polymer shell can be controlled. In one embodiment, the polymer shell is less than about 100 nm thick. In another embodiment, the polymer shell is less than 50 nm thick. In still another embodiment, the polymer shell is between about 25 nm and about 100 nm thick.

The diameter of the capsule may also vary. It is envisioned that capsules having a diameter less than about 1 micrometer may be synthesized. In one example, a majority of the diameters of the capsules are between about 200 nm and about 800 nm.

BRIEF DESCRIPTION OF THE DRAWINGS

FIG. 3a is a Transmission Electron Microscope (TEM) image of ~300 nm liquid-core polymer capsule with ~50 nm thick polymer shell using thermal initiation.

FIG. 3b is a TEM image of ~300 nm liquid-core polymer capsule with ~25 nm thick polymer shell formed by halving the monomer concentration used in FIG. 3a.

FIG. 3c is a TEM image of ~300 nm liquid-core polymer capsules with ~40 nm thick polymer shells using UV initiation.

DETAILED DESCRIPTION OF THE INVENTION

Figure 1:
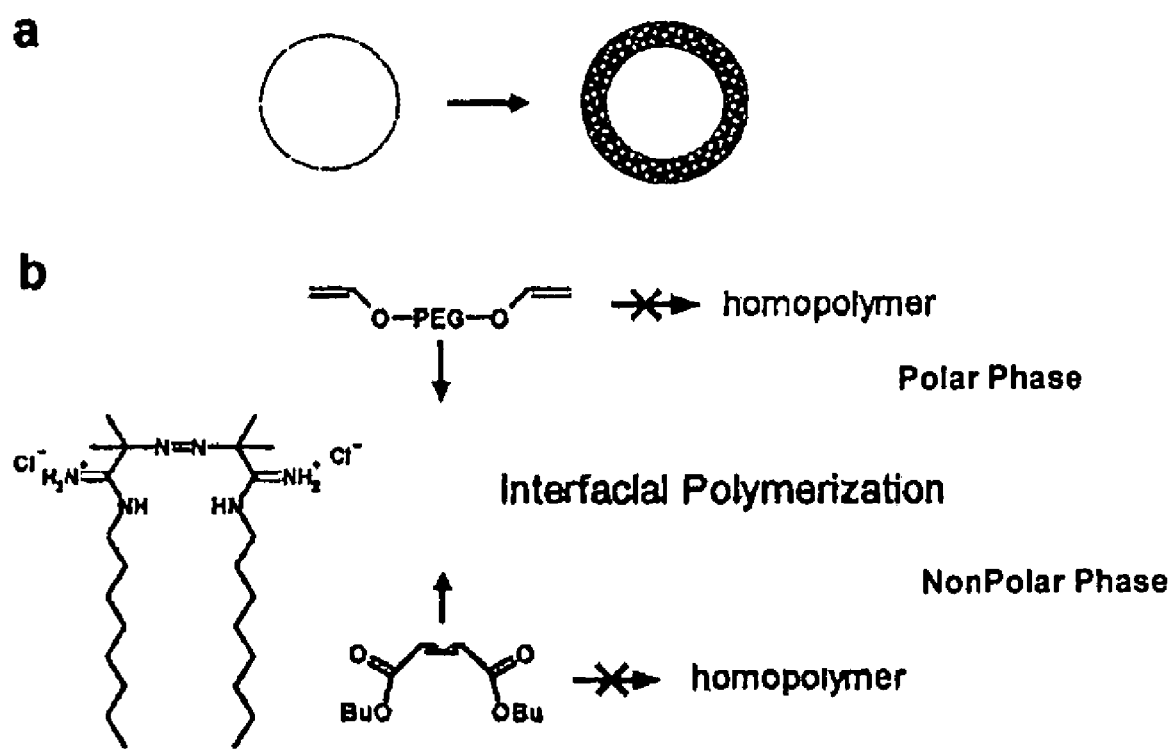
FIG. 1a is a schematic representation of the interfacial free radical polymerization of emulsion non-polar solvent drops to form liquid core capsules.
FIG. 1b is a schematic representation of the interfacial alternating copolymerization of hydrophilic PEG-divinyl ether and hydrophobic dibutyl maleate initiated with an a surface active initiator at the polar/non-polar interface.

The present invention is directed towards the use of interfacial free radical alternating copolymerization, which allows for precise control of the onset of reaction, leading to the direct encapsulation of sub-micron liquid drops within uniform nanometer thick polymer shells. Conceptually, this approach is analogous to interfacial condensation polymerizations, but relies on the alternating free radical copolymerization of a hydrophobic monomer, such as a maleate, and a hydrophilic monomer such as a vinyl ether monomer, initiated by a surface-active initiator, such as an azo-initiator, to localize radical formation at the polar/non-polar interface.

In the interfacial free radical alternating copolymerization process, monomers, depending on the type of conjugation of double bonds and functional groups, can be categorized into two major groups: electron-acceptor or hydrophobic monomers and electron-donor or hydrophilic monomers. Electron-acceptor monomers may include, but are not limited to functional substituted ethylenes, containing primary carboxyl, anhydride, ester, amide, imide and nitryl components. Electron-acceptor monomers also include dibutyl maleate, imides and N-substituted imides of unsaturated dicarboxylic acids, unsaturated mono- and dicarboxylic acids, and tetrahalogen-substituted ethylenes such as maleic anhydride and its α,β-substituted derivatives. The electron-donor monomers which copolymerize with the electron-acceptor monomers comprise a wide array of monomers and may include, but are not limited to, divinyl ethers, divinyl sulfides, divinyl amines, divinyl esters, divinylarylenes, diallylarylenes, conjugated dienes, nonconjugated dienes, cyclodienes, and vinyl and allyl esters of unsaturated mono- and dicarboxylic acids. The use of hydrophobic and hydrophilic variants of electron-acceptor and electron donor monomers that alternately polymerize, but individually do not homopolymerize is an aspect of this embodiment. One or both of the monomers may be unsaturated.

In the present invention, the hydrophobic monomers may be solubilized in non-polar solvents (i.e., solvents whose molecules do not have a dipole), while the hydrophilic monomers may be solubilized in polar solvents (solvents whose molecules have a dipole). Non-polar solvents include, but are not limited to, $C_4$-$C_{25}$ aliphatic alkanes as well as monocyclic, polycyclic and heterocyclic arenes. Non-limiting examples of non-polar solvents include, pentane, hexane, hexadecane, benzene, toluene, styrene, naphthalene, pyridine, pyrrole, and furan. The polar solvents include, but are not limited to, protic and aprotic solvents. Examples of polar protic solvents include water, alcohols, and carboxylic acids. Examples of polar aprotic solvents include dimethyl sulfoxide and N,N-dimethylformamide. To facilitate the polymerization process, the use of a surfactant may be used to reduce interfacial tension between the polar and non-polar phases.

Along with the hydrophobic and hydrophilic monomers used in the free radical alternating copolymerization process, an initiator is used to begin the polymerization process. Popular initiators include the use of dyes and peroxides. Dye-sensitized polymerization is well known in the chemical literature. While not wishing to be bound by theory, after absorbing laser light, the dye is believed to be excited to a triplet state. The triplet state reacts with a tertiary amine such as the triethanolamine, producing a free radical, which initiates the polymerization reaction. Polymerization is extremely rapid and is dependent on the functionality of the macromer and its concentration, light intensity, and the concentration of dye and amine. Any dye can be used which absorbs light having a frequency between 320 nm and 900 nm, can form free radicals, is at least partially water soluble, and is non-toxic to the biological material at the concentration used for polymerization. There are a large number of photosensitive dyes that can be used to optically initiate polymerization, such as ethyl eosin, eosin Y, fluorescein, 2,2-dimethoxy-2-phenyl acetophenone, 2-methoxy,2-phenylacetophenone, camphorquinone, rose bengal, methylene blue, erythrosin, phloxime, thionine, riboflavin, methylene green, acridine orange, xanthine dye, and thioxanthine dyes. Alternatively, thermally activatable initiators may be used.

In the present invention, an activated interfacial free radical initiator may be used. More specifically, the interfacial free radical initiator may be an azo compound (a compound containing a nitrogen-nitrogen double bond), such as 2,2'-azobis (N-octyl-2-methyl-propionamidine) dihydrochloride. This azo compound, rather than being solely water-soluble or solvent-soluble, has a hydrophobic portion and a hydrophilic portion, which allows it to act as an interfacially active initiator allowing the polymerization process to take place at or near the interface of the polar and non-polar solvents. Acceptable initiators containing a hydrophobic portion and a hydrophilic portion are not limited to azo dyes however.

Figure 2:
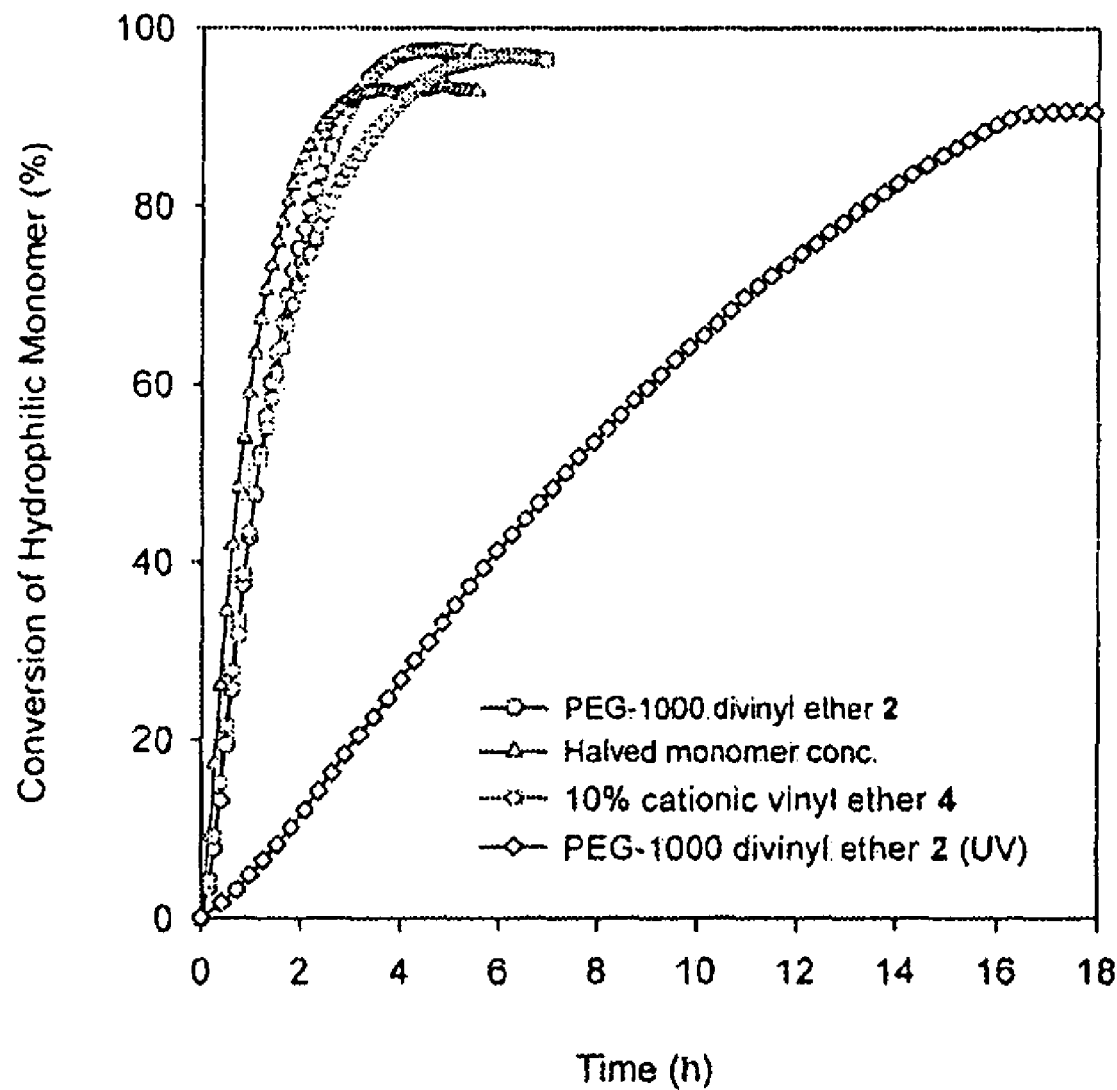
FIG. 2 is a diagram summarizing polymerization kinetics of emulsions.

An example of the interfacial free radical alternating copolymerization process of the present invention may be described with references to the Figures. As seen in FIG. 1, emulsions used in these studies were prepared from a 10 wt % non-polar phase composed of hexadecane, 25 wt % dibutyl maleate (hydrophobic monomer), and 5% paraffin wax (hydrophobe), and a polar phase containing PEG-1000 divinyl ether (hydrophilic monomer with the concentration of vinyl groups fixed equimolar to dibutyl maleate), and 1 wt % of dodecyltrimethylammonium bromide (DTAB) as surfactant. Following homogenization and high shear dispersion (sonication) of the non-polar/polar mixture, the emulsion system was polymerized at 60° C. via injection of an interfacially active free radical initiator, 2,2'-azobis(N-octyl-2-methyl-propionamidine) dihydrochloride ($t_{1/2}$=10 hr. at 59.5° C.), as an aqueous solution. The reaction was monitored by absolute heat-flow calorimetry (CPA 200, Chemisens AB) until completion after ~4 hours (FIG. 2, circles). Polymerization resulted in polymer-encapsulated oil droplets.

Figure 9:
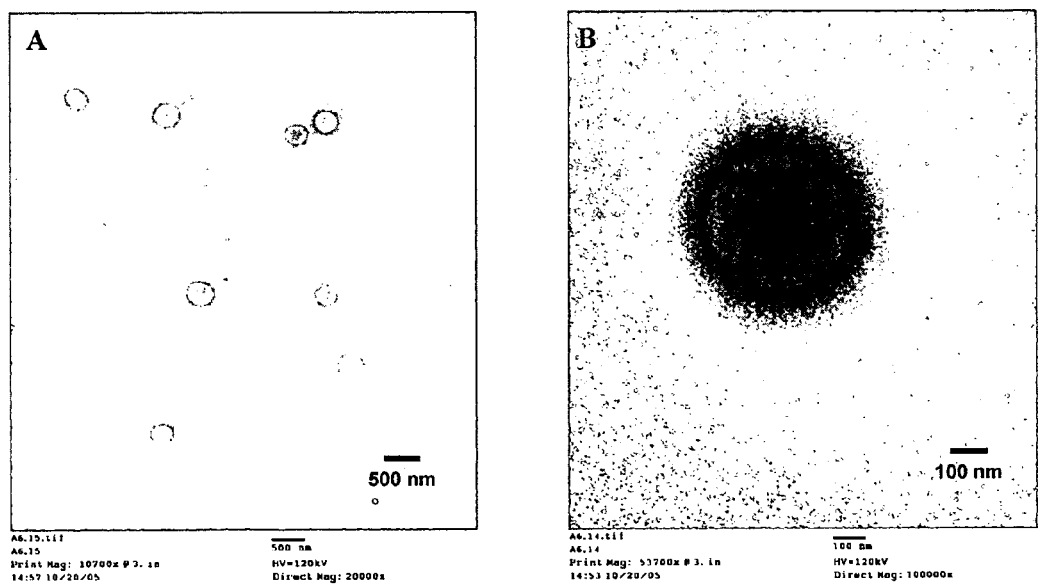
FIG. 9A is a transmission electron microscopy (TEM) image of sub-micron aqueous-core capsules at 20,000× magnification (reference bar equals 500 nm).
FIG. 9B is a transmission electron microscopy (TEM) image of sub-micron aqueous-core capsules at 100,000× magnification (reference bar equals 100 nm).

Although interfacial free radical copolymerizations, as described here, are limited to monomer pairs that alternately copolymerize, the ester and ether functionalities of maleate and vinyl ether monomers are prime candidates for functionalization with a rich variety of biologically or chemically active groups. For example, when 10 wt % of PEG divinyl ether monomer is replaced with a cationic vinyl ether (N-ethyl-N,N-dimethyl-2-(vinyloxy)ethylammonium chloride) the reaction is slightly retarded beyond 70% conversion, presumably due to the build-up of charge and reduced diffusion rate of monomers into the polymerizing interface. Nevertheless, the reaction approaches full conversion within ~6 hours (FIG. 2, squares) and the size, morphology and shell thickness of the resulting liquid-core capsules are very similar to liquid-core capsules formed without cationic monomer. Nevertheless, the size, morphology and shell thickness of the resulting liquid-core capsules with or without cationic monomer, appear similar when imaged under TEM (FIG. 9a). No polymerization is observed when either the hydrophobic or hydrophilic monomer is absent; thus, the thickness of the polymer shell can be controlled by limiting the concentration of either monomer. Polymer capsules may also be formed using vinyl ethers with amine, carboxylic, and other chemical groups to which biologically active groups can be conjugated for site-directed drug delivery.

The overall size of the capsules is set by the processing conditions used to form the initial emulsion. Under thermal reaction conditions (60° C.), the emulsion drops, formed at room temperature, are partially destabilized and coalesce, forming larger capsules. Number-size analysis of dynamic light scattering (DLS) measurements yields a bimodal size distribution containing a large population (73%) of submicron capsules with an average diameter of 218±15 nm and a small population (27%) of larger capsules with an average diameter of 745±41 nm. The slightly larger size (~290 nm and 775 nm for small and large capsules respectively) and slight elongation observed under TEM is likely due to flattening and deformation of the capsules during drying.

Destabilization and coalescence, encountered under thermal reaction conditions, may be avoided by conducting polymerizations at lower temperatures (35° C.), using 150 W UV irradiation at 365 nm (BIB-150P, Spectronics Corp.) to initiate the reaction. While the kinetic data (FIG. 2, diamonds) shows a significant decrease in the reaction rate, presumably due to the decreased propagation rate constant and the inability of light to deeply penetrate the opaque emulsion system, analysis of the capsules formed by DLS shows a monomodal size distribution of capsules with an average number-weighted diameter of 186±23 nm. This relatively monodisperse size distribution of liquid-core capsules is consistent with the typically narrow droplet size distribution of the starting emulsion. As expected, imaging by TEM shows particles with an average diameter of 240 nm (FIG. 3c), slightly larger than those measured by DLS. The liquid core capsules of the present invention may be less than 800, 700, 600, 500, 400, or 300 nm in diameter. In one particular embodiment, the liquid core capsules are between about 200 nm and about 800 nm in diameter.

Other approaches to the direct formation of liquid-core capsules have been conducted using monomers dissolved and initiated within a dispersed oil phase. When the polymer formed is insoluble in the oil and specific wetting conditions at the polymer/oil and polymer/water interfaces are satisfied, the polymer precipitates to form an engulfing shell around the oil drops. However, previous studies demonstrate that these approaches often yield non-uniform shell morphologies, solid particles, and intercapsule bridging the extent of which are highly sensitive to the monomers, surfactants, and initiators used.

Assuming equal densities for the monomers, solvents, and polymer, the thickness (t) of the polymer shell is related to the core diameter (d) by:

$$t = \left\{ \left[ 1 + \frac{\alpha}{1-\alpha} \left( \frac{MW_{VE}}{2MW_{DBM}} + 1 \right) \right]^{\frac{1}{3}} - 1 \right\} \frac{d}{2}$$

Figure 3:
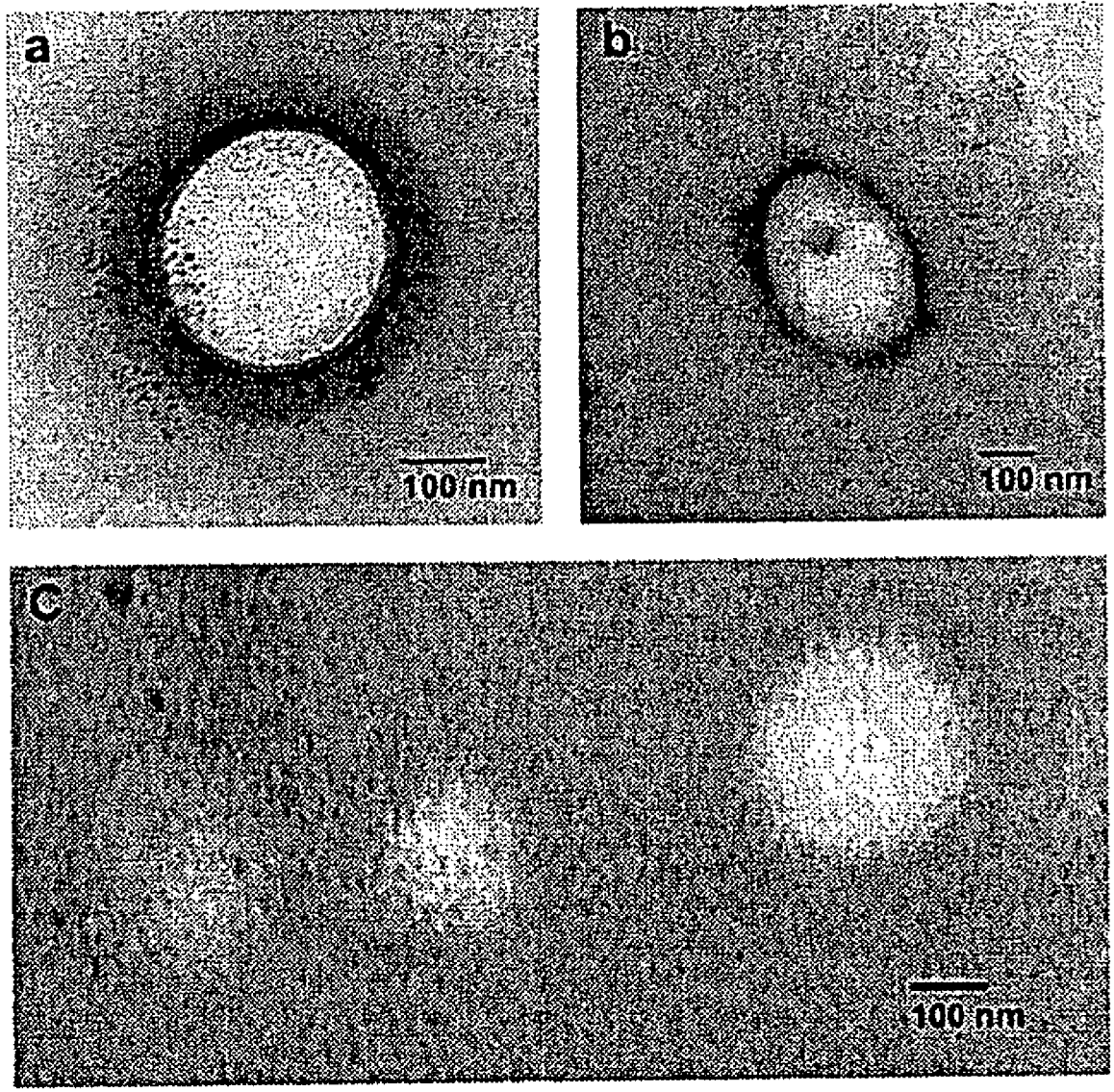

Here, $\alpha$ is the weight fraction of dibutyl maleate in the non-polar phase and $MW_{VE}$ and $MW_{DBM}$ are the molecular weights of the PEG vinyl ether and dibutyl maleate respectively. For the capsules shown in FIG. 3, with core diameters of ~200 nm, the calculated shell thicknesses that should result for $\alpha$=0.25 and $\alpha$=0.125 are 28 nm and 14 nm, respectively. This prediction is borne out experimentally where it is observed that halving the loading of dibutyl maleate, also halves the shell thickness (FIG. 3). As would be expected from their more flexible shells, thinner wall capsules reveal shells (~50 nm and ~25 nm) that are thicker than the theory predicts; however, much of this discrepancy could be the result of capsule deformation coupled with the TEM imaging geometry.

The overall size of the capsules is set by the processing conditions used to form the starting emulsion drops. Number-size analysis of dynamic light scattering measurements show that consistent processing conditions result in capsules with almost constant number-average diameters of ~220 nm and relatively low polydispersity, standard deviation ~15 nm.

The fundamental relation governing the rate of monomer conversion (χ) for interfacial polymerization in emulsions follows closely that for traditional emulsion polymerizations:

$$\frac{dx}{dt} = \frac{k_p C_p \bar{n} N_c}{n_M^o N_A}$$

Here, $k_p$ and $C_p$ correspond to the mean polymerization rate constant and concentration of the two monomers at the locus of polymerization within the interface; $\bar{n}$ is the average number of active radicals within the interface of the capsules; $N_c$ is the number of capsules; $n_M^o$ is the concentration of monomer in the entire system; and $N_A$ is Avogadro's number. Halving the loading of dibutyl maleate and PEG divinyl ether ($n_M^o$), results in a concomitant decrease in Cp, and for a fixed partition constant, no change in the rate of conversion is expected. However, since the concentration of surface-active radical initiator is fixed whereas the volume of the polymerizing interface is halved at any conversion, $\bar{n}$ increases, and this explains the faster rate of conversion observed when the loading of the two monomers is halved (FIG. 3).

Owing to the low solubilities of the hydrophilic monomers in the non-polar phase and the hydrophobic monomer in the polar phase as seen in FIG. 1, the free radical polymerizations described here are constrained to the interfaces due to the alternating nature of the copolymerization and the reluctance of either monomer to radically homopolymerize. Thus, in contrast to other interfacial polymerizations that "grow" polymers out from surfaces, this approach leads to a polymerizing interface that grows from within. An example of interfacial polymerizations that "grow" polymers out from surfaces, encapsulation is performed by first extruding a cell suspension to form a liquid core, then surrounding the cell droplet by a polymer solution to form a liquid shell, followed by the extraction of the polymer solvent to precipitate a solid shell.

The position of highest radical activity within the polymerizing interface is set by the relative diffusion rates of the hydrophobic and hydrophilic monomers to the active radical ends, allowing for uniform shell thicknesses as the monomers will diffuse, and react, more readily at thin portions of the shell compared to thicker portions. Because the polymerization occurs within the interface, intercapsule bridging polymerization is also not a concern and reactions can be carried out at high concentrations.

The example above describes an interfacial free-radical alternating copolymerization approach to encapsulate oil drops in a polymer shell of dibutyl maleate and PEG divinyl ether. It is also possible to apply interfacial polymerizations to encapsulate water drops in a polymer shell as demonstrated by the following examples.

Figure 4:
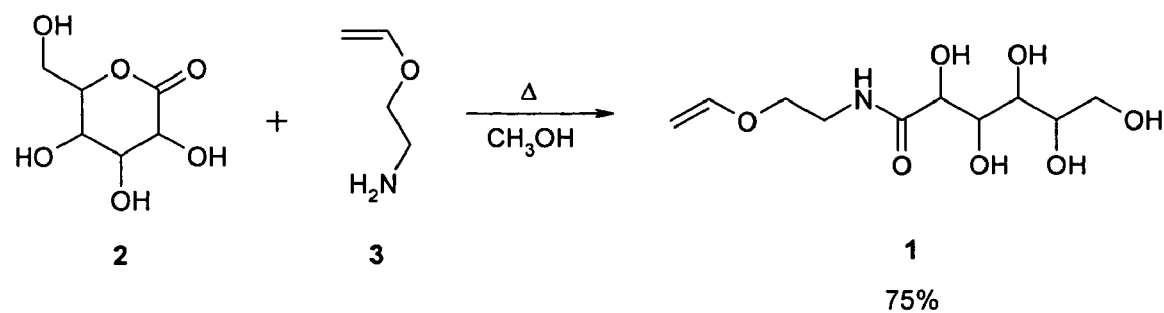
FIG. 4 is a chemical reaction showing the synthesis of vinyl gluconamide by aminolysis of δ-gluconolactone with aminoethyl vinyl ether.
Figure 5:
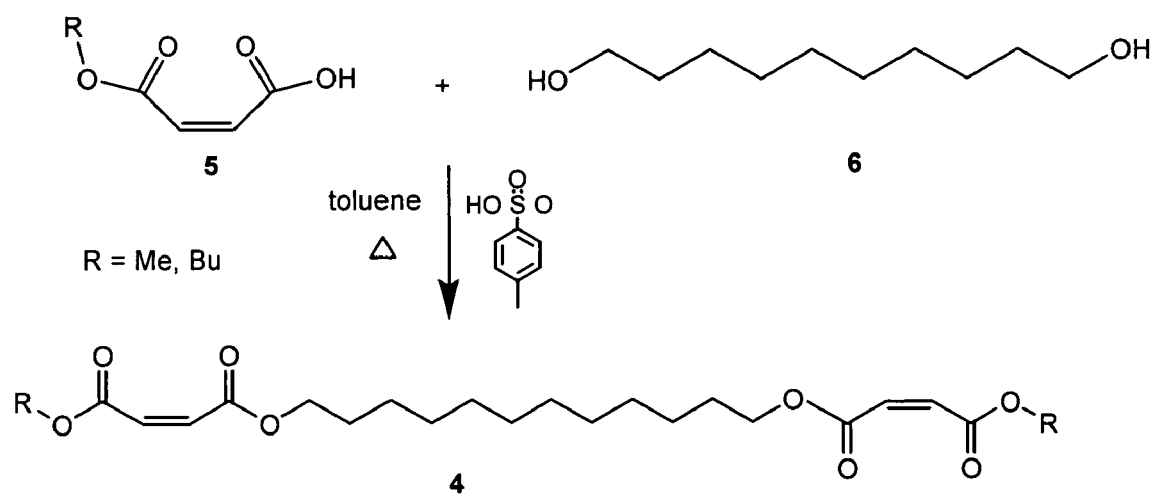
FIG. 5 is a chemical reaction showing the synthesis of 12-{[2Z]-4-Butoxy-4-oxobut-2-enoyl}-dodecyl butyl (2Z)-but-2-enedioate (4), an oil soluble crosslinker, by the reaction of monobutyl maleate with dodecandiol.

Vinyl gluconamide (1) was prepared in 75% yield via the aminolysis of δ-gluconolactone (2) with aminoethyl vinyl ether (3) in refluxing methanol, followed by recrystallization, as shown schematically in FIG. 4. 12-{[2Z]-4-Butoxy-4-oxobut-2-enoyl}-dodecyl butyl (2Z)-but-2-enedioate (4), an oil soluble crosslinker, was prepared via monobutyl maleate (5) with dodecandiol (6) with in refluxing toluene with the exiting of p-toluenesulfonic acid followed by washing steps, as shown in FIG. 5.

In one example, an aqueous (polar) phase was prepared containing vinyl gluconomide (1.0 g, 3.8 mmol), 0.1% sodium chloride in water (9.0 g). An oil phase (non-polar) phase was prepared containing dibutyl maleate (0.91 g, 3.6 mmol, Acros Organics), dibutyl maleate-based crosslinker (0.043 g, 0.2 mmol), sorbitan monooleate (Span 80, Sigma-Aldrich Chemical Co.), block co-polymer stabilizer (Hypermer B246SF, Uniqema) and decane (39.1 g). Hypermer B246SF consists of a hydrophobic polyhydroxy fatty acid portion and a hydrophilic polyethylene glycol block portion. In another example, the aqueous (polar) phase was prepared with vinyl gluconomide (0.95 g, 3.6 mmol), Poly (ethylene glycol) (PEG) divinyl ether (MW 240, 0.05 g, 0.2 mmol, Sigma-Aldrich Chemical Co.), 0.1% sodium chloride in water (9.0 g) and an oil (non-polar) phase was prepared with dibutyl maleate (0.912 g, 4.0 mmol), Span 80, Hypermer B246SF, and decane (39.1 g).

Inverse (water in oil) miniemulsions (50 g) were prepared by homogenizing (24,000 rpm) the aqueous and oil phases, containing the monomers, NaCl, surfactant, and polymeric stabilizer, for 100 min followed by 30 min of sonication (278 W, 2.5 s pulses separated by 1 s intervals). The inverse miniemulsions were then transferred to an absolute heat flow reaction calorimeter to monitor the polymerization kinetics. Reactions were initiated thermally at 60° C. via injection of an oil solution of azo-initiator, V601 (0.1 g, 0.43 mmol) in 1.0 g decane. Kinetic data was collected for 18 hours and the extent of vinyl ether conversion was calculated from the vinyl ether/dibutyl maleate copolymerization enthalpy (61.1 kJ/mol). This enthalpy of copolymerization was calorimetrically measured from solution polymerizations of equimolar mixtures of ethylene glycol vinyl ether and dibutyl maleate in toluene whose final conversion was gravimetrically determined.

Figure 6:
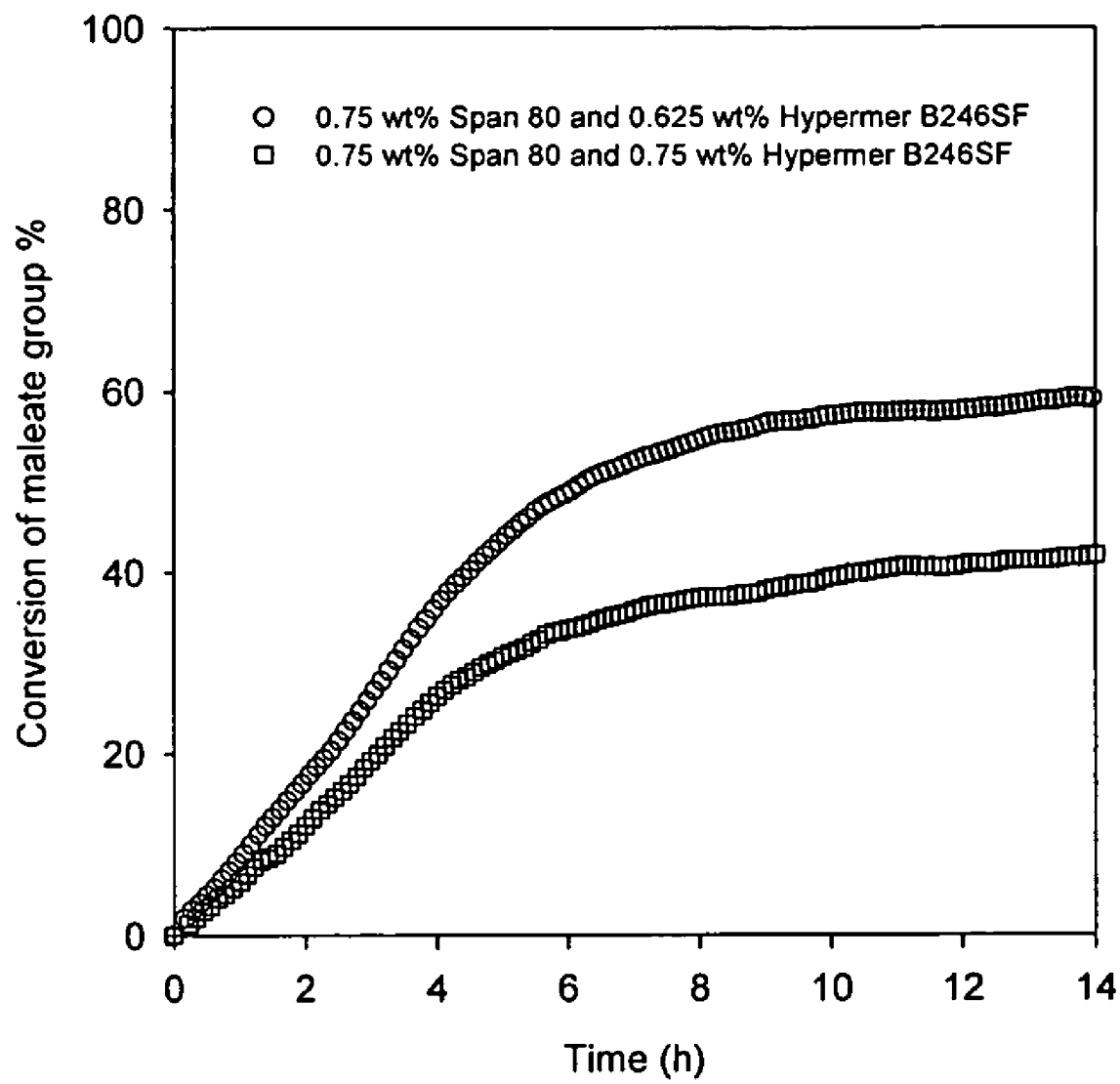
FIG. 6 is a graph showing the kinetics of interfacial copolymerization of vinyl gluconamide, dibutyl maleate and dimaleate crosslinker.
Figure 7:
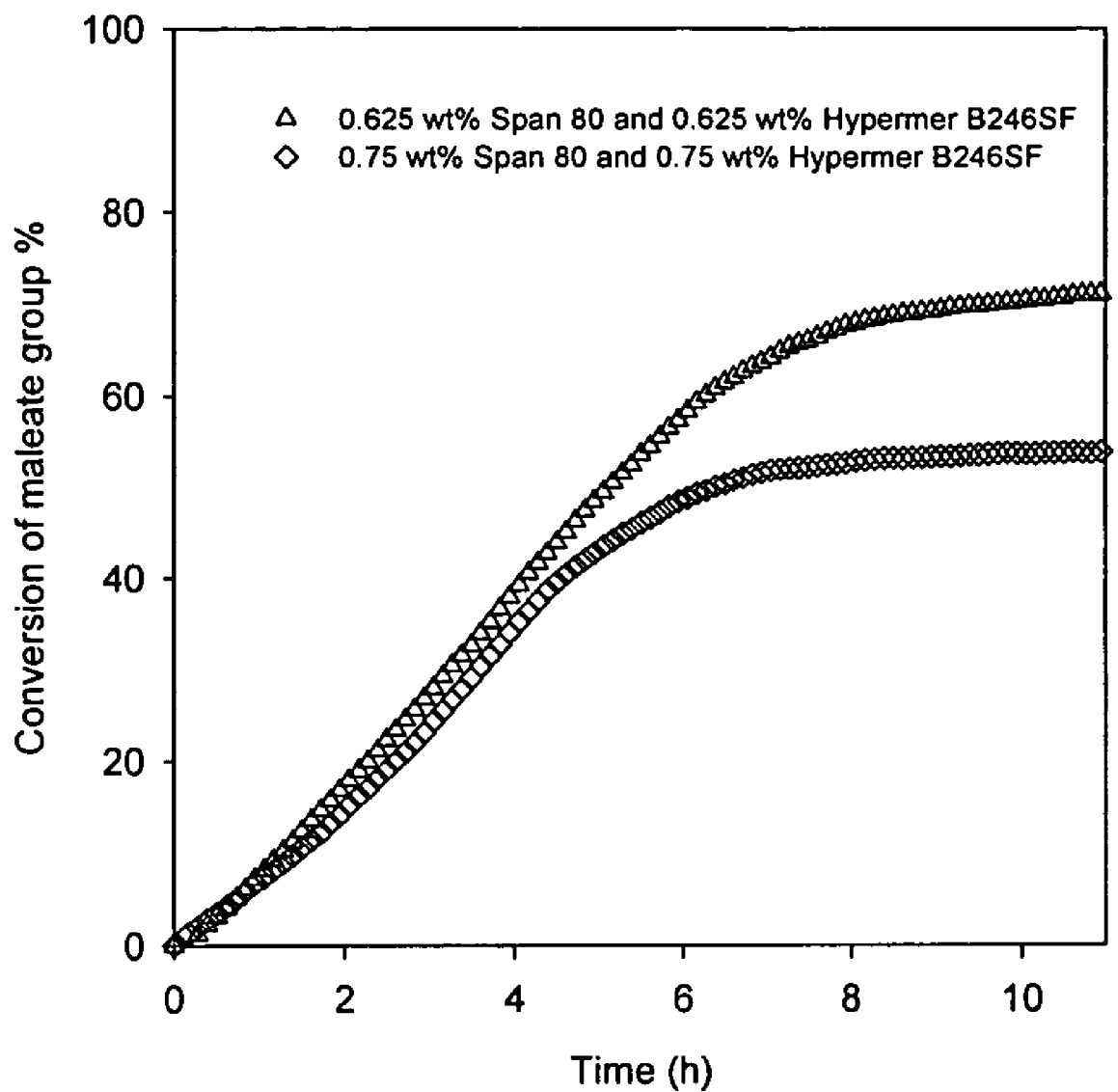
FIG. 7 is a graph showing the kinetics of interfacial copolymerization of vinyl gluconamide, dibutyl maleate and PEG divinyl ether as crosslinker.

The polymerization kinetics of miniemulsion polymerizations with the oil-soluble (dibutyl maleate based) cross-linker are shown in FIG. 6 for 2 loadings of the Hypermer polymeric stabilizer. The reactions reach approximately 40% and 60% conversion, and with increasing amounts of the polymeric stabilizer, the ultimate conversion decreases. Similar results are observed when a water-soluble cross-linker, PEG divinyl ether (MW 240), is used in place of an oil-soluble cross-linker (FIG. 7). The ultimate conversion decreases with increasing amounts of the surfactant and polymeric stabilizer. Although not wishing to be bound by theory, addition of the block copolymer surfactant is believed to hinder the diffusion of the two monomers to the polymerizing interface.

Figure 8:
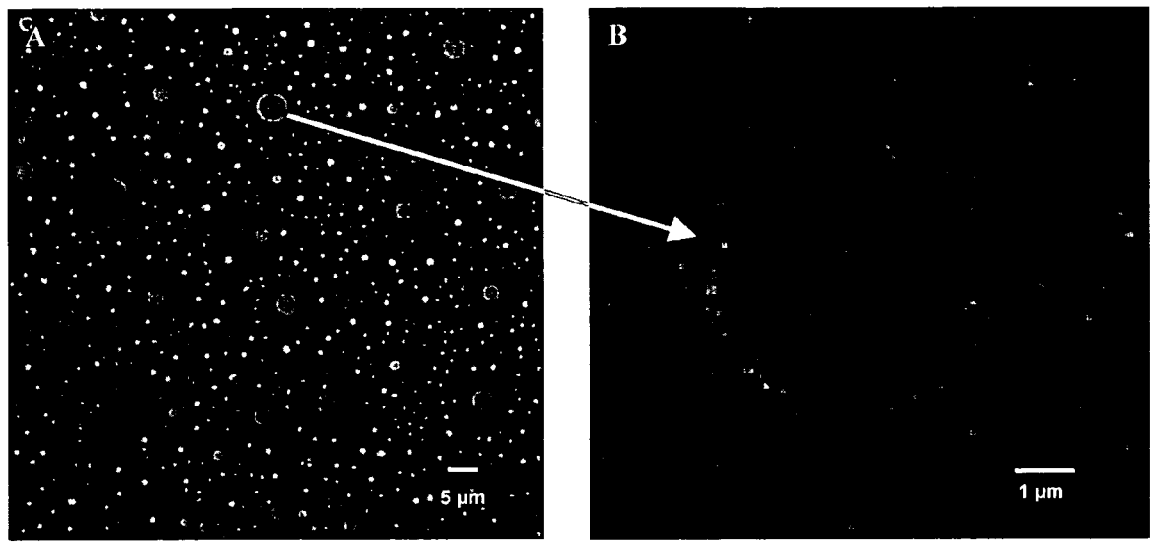
FIG. 8A is a fluorescence image of dehydrated aqueous-core capsules.
FIG. 8B is a confocal image of the horizontal cross section of the particle shown by the arrow in FIG. 8A.

To confirm the formation of a liquid-core structure, a water-soluble dye, Rhodamine B, was added into the aqueous phase of a final composition containing 0.75 wt % Span 80 and 0.75% Hypermer B 246SF as previously described above and shown in FIG. 7. After polymerization, the sample was diluted 100× with hexane and air dried prior to imaging using a laser scanning confocal microscope. As shown in the image in FIG. 8A, the size distribution is bimodal with both large (>1 micron) and sub-micron capsules. For the larger capsules, cross-sectional imaging (FIG. 8B), confirms the presence of a well-defined polymer shell into which Rhodamine B precipitates following dehydration. For the sub-micron capsules (FIGS. 9A and 9B), transmission electron microscopy (TEM) confirms the presence of a defined polymer shell structure. For these images, the sample was diluted 100× with hexane, placed on a copper grid coated with 10-mesh Formvar (Electron Microscopy Sciences), blotted gently with filter paper to a thin film spanning the grid and vacuum dried for two days at room temperature. No contrast agents were utilized. These results demonstrate the interfacial free-radical alternating copolymerization technique can also be used to form aqueous-core polymer capsules.

In conclusion, a direct and scalable approach has been shown for encapsulating sub-micron liquid drops within less than about 100 nm thick polymer shells through the free radical alternating copolymerization of hydrophobic and hydrophilic monomers at interfaces. Shell thickness and overall capsule size can be finely tuned by adjusting monomer concentration and the processing conditions used in preparing the starting emulsion drops. The general principle of the interfacial free radical alternating copolymerization has many potential applications extending beyond the preparation of liquid-core capsules and into other established nanotechnologies where the preponderance of interfaces accentuates the significance of this polymerization technique.

Based on the foregoing disclosure, it should now be apparent that the encapsulation of liquid core capsules of the present invention will carry out the objects set forth hereinabove. This interfacial free radical copolymerization method for preparing liquid-core capsules eliminates procedures and materials, such as repeated centrifugation/washing, sintering, core-removal, microphase separation, vesicle templates, and block copolymers, that limit control of shell thickness or large-scale practical application of existing capsule preparation techniques. In this way, it is envisioned that the present invention provides a drug delivery system wherein a drug is located within a liquid core capsule, wherein the capsule comprises a polymer shell which is a reaction product of a hydrophobic monomer and a hydrophilic monomer. It is, therefore, to be understood that any variations evident fall within the scope of the claimed invention and thus, the selection of specific component elements can be determined without departing from the spirit of the invention herein disclosed and described.

What is claimed is:

1. A method of encapsulating a liquid material, the method comprising the steps of:
   providing a mixture comprising a non-polar solution containing at least one hydrophobic monomer and a non-polar solvent, and a polar solution containing at least one hydrophilic monomer and a polar solvent, wherein the non-polar solution and the polar solution are not miscible in each other;
   homogenizing the mixture to form an emulsion comprising droplets of non-polar solution in the polar solution or droplets of polar solution in the non-polar solution; and
   polymerizing the hydrophobic monomer and the hydrophilic monomer with an initiator that initiates an interfacial free radical alternating copolymerization process, forming a polymer shell around the droplets, wherein the polymer shell around the droplets is the reaction product of the hydrophobic monomer alternately copolymerizing with the hydrophilic monomer; wherein at least one of the hydrophobic monomer and the hydrophilic monomer is unsaturated; and
   wherein the hydrophilic monomer is selected from the group consisting of divinyl ethers, divinyl sulfides, divinyl amines, divinyl esters, divinylarylenes, diallylarylenes, conjugated dienes, nonconjugated dienes, cyclodienes, vinyl and allyl esters of unsaturated mono- and dicarboxylic acids, and mixtures thereof; and
   wherein the hydrophobic monomer is selected from the group consisting of dibutyl maleate, maleic anhydride and its $\alpha,\beta$-substituted derivatives, imides and N-substituted imides of unsaturated dicarboxylic acids, unsaturated mono- and dicarboxylic acids, and tetrahalogen-substituted ethylenes.

2. The method of claim 1, wherein the alternating copolymerization process is constrained to proceed in a region of an interface between the polar and non-polar solutions.

3. The method of claim 1, wherein neither the hydrophobic monomer nor the hydrophilic monomer substantially homopolymerize.

4. The method of claim 1, wherein the thickness of the polymer shell is adjustable by alternating the concentration of at least one of the hydrophobic monomer and the hydrophilic monomer.

5. The method of claim 1, wherein the thickness of the polymer shell is less than about 100 nanometers (nm).

6. The method of claim 1, wherein the initiator is an azo compound.

7. The method of claim 1, wherein the initiator has a hydrophobic portion and a hydrophilic portion.

8. The method of claim 1, wherein the initiator is activated by irradiation or heat.

9. The method of claim 1, wherein the mixture further comprises a surfactant.

10. The method of claim 8, wherein the initiator is activated by irradiation at a temperature less than about 60° C.

11. The method of claim 10, wherein the temperature is about 35° C.

* * * * *